United States Patent
Jallon (10) Patent No.: US 9,489,600 B2
(45) Date of Patent: Nov. 8, 2016

(54) SYSTEM AND METHOD FOR DETERMINING THE ACTIVITY OF A MOBILE ELEMENT

(75) Inventor: Pierre Jallon, Grenoble (FR)

(73) Assignees: Commissariat A L'energie Atomique et Aux Energies Alternatives, Paris (FR); Movea, Grenoble (FR)

( * ) Notice: Subject to any disclaimer, the term of this patent is extended or adjusted under 35 U.S.C. 154(b) by 1204 days.

(21) Appl. No.: 13/266,094

(22) PCT Filed: Apr. 26, 2010

(86) PCT No.: PCT/EP2010/055560
§ 371 (c)(1),
(2), (4) Date: Mar. 8, 2012

(87) PCT Pub. No.: WO2010/122172
PCT Pub. Date: Oct. 28, 2010

(65) Prior Publication Data
US 2012/0158351 A1 Jun. 21, 2012

(30) Foreign Application Priority Data

Apr. 24, 2009 (FR) ................................. 09 52690

(51) Int. Cl.
*G01P 15/18* (2013.01)
*G06F 15/00* (2006.01)
(Continued)

(52) U.S. Cl.
CPC ............ *G06K 9/6297* (2013.01); *A61B 5/1101* (2013.01); *A61B 5/1116* (2013.01); *A61B 2562/0219* (2013.01)

(58) Field of Classification Search
CPC .......... G06K 9/6297; A61B 256/0219; A61B 5/1101
USPC ......................................................... 702/141
See application file for complete search history.

(56) References Cited

U.S. PATENT DOCUMENTS

2005/0234309 A1   10/2005   Klapper
2006/0064037 A1   3/2006    Shalon et al.
(Continued)

OTHER PUBLICATIONS

Paul-Valentin Borza, Motion-based Gesture Recognition with an Accelerometer, Babes-Bolyai of Cluj-Napoca, Jul. 2008.*
(Continued)

*Primary Examiner* — Michael Nghiem
*Assistant Examiner* — Peter Ngo
(74) *Attorney, Agent, or Firm* — Stroock & Stroock & Lavan LLP (57) ABSTRACT

A system for determining activity of a mobile element, includes at least one motion sensor having a measurement axis, and which is securely connected to the mobile element. A filter for selects, for each measurement axis of the motion sensor, high frequencies above a first threshold, and processing equipment for determines a unidimensional high-frequency component (y(n)) equal to the square of the Euclidean norm of the high frequencies along the measurement axes of the motion sensor. A calculator calculates, for each state, probability density functions (Py,i) of the high-frequency component, the probability density function corresponding to each state according to a Chi-square law with a degree of freedom equal to the number of measurement axes of the motion sensor. An analyzer defines states of the mobile element, utilizing the probability density function of the high-frequency component for each state, together with the probabilities of transitions between two successive states.

8 Claims, 3 Drawing Sheets

(51) Int. Cl.
*G06K 9/62* (2006.01)
*A61B 5/11* (2006.01)

(56) References Cited

U.S. PATENT DOCUMENTS

| | | | | |
|---|---|---|---|---|
| 2007/0250286 | A1* | 10/2007 | Duncan | A61B 5/1121 702/139 |
| 2007/0276278 | A1* | 11/2007 | Coyle et al. | 600/529 |
| 2008/0004904 | A1 | 1/2008 | Tran | |
| 2009/0021858 | A1* | 1/2009 | Fu et al. | 360/99.01 |
| 2009/0137933 | A1* | 5/2009 | Lieberman | A61B 5/1036 600/595 |
| 2009/0260426 | A1* | 10/2009 | Lieberman et al. | 73/65.01 |

OTHER PUBLICATIONS

Seemant Teotia, Appendix B Chi Square Distribution of "Saddlepoint Approximation for Calculating Performance of Spectrum-Sliced WDM System", Virginia Polytechnic Institude and State University, Jul. 1999.*

Lawrence R. Rabiner, A tutorial on Hidden Markov Models and Selected Applications in Speech Recognition, Feb. 1989, IEEE.*

Veltink, "Detection of Static and Dynamic Activities Using Uniaxial Accelerometer", 1996.*

Daubney B et al.: "Estimating Gait Phase using Low-Level Motion", Motion and Video Computing, 2008, p. 1-6.

Pfau et al.: "A Hidden Markov model-based stride segmentation technique applied to equine inertial sensor trunk movement data", Journal of Biomechanics, Dec. 19, 2007, pp. 216-220.

International Search Report and Written Opinion dated Jul. 23, 2010, issued in counterpart International Application No. PCT/EP2010/05560.

* cited by examiner

SYSTEM AND METHOD FOR DETERMINING THE ACTIVITY OF A MOBILE ELEMENT

CROSS-REFERENCE TO RELATED APPLICATIONS

This application is a national phase application under §371 of PCT/EP2010/055560, filed Apr. 26, 2010, which claims priority to French Patent Application No. 0952690, filed Apr. 24, 2009 both of which are incorporated herein by reference.

BACKGROUND OF THE INVENTION

1. Field of the Invention

The present invention relates to a system and to a method for determining the activity of a mobile element.

2. Description of the Prior Art

Systems and methods for analyzing movement based on a hidden Markov model are known, such as that described for example in the documents "Gesture recognition using the XWand" by Daniel Wilson and Andy Wilson and "Motion-based gesture recognition with an accelerometer" (bachelor's thesis) by P. V. Borza.

The document "A hidden Markov model-based stride segmentation technique applied to equine inertial sensor trunk movement data", Journal of Biomechanics 41 (2008) 216-220 by Thilo Pfau, Marta Ferrari, Kevin Parsons and Alan Wilson relates to the analysis of striding horses.

However, these systems and methods are of limited precision.

BRIEF DESCRIPTION

One object of the invention is to improve the precision in determining the activity of a mobile element, particularly for a living being, whether human or animal.

According to one aspect, the invention provides a method for determining the activity of a mobile element (EM), said mobile element having at least one motion sensor (CM) with at least one degree of freedom substantially affixed to said mobile element (EM), wherein:
- a signal S(n) is measured at discrete times from zero to N when the mobile element is in a state E(n);
- a series of values q(n) is observed which is a function of the signal S(n);
- a list of the most likely states $E(k_i)$ is determined from the calculation of:
  - a probability function of q(n) when the mobile element is in the E(n) state;
  - a probability function of a transition from the E(n-1) state to the E(n) state;
  - probability functions of each state of the mobile element at time zero.

It is noted that a hidden Markov model can be defined by two random processes: a first one is called the "state" in the present application and is not observed, or in other words is one which is hidden, and a second one which is the observation, the probability density function of which at a given instant depends on the value of the state at the same instant. According to this first aspect of the invention, the state takes discrete values, i.e. 0 corresponding to the presence of oscillations and 1 to the absence of oscillations.

The norm used may for example be the sum of the squares of the high frequencies along the measurement axes of the motion sensor that are taken into account or the square of the Euclidean norm of the high frequencies along the measurement axes of the motion sensor that are taken into account.

A motion sensor is one of which the signal variations are representative of the movement.

Such a system makes it possible to analyze the activity of a mobile element with greater precision. Specifically, by taking into account the high-frequency component it is possible to use additional information which enables small movements of the sensor, or in other words oscillations or vibrations, such as trembling, to be detected.

The signal produced by the motion sensor at the instant n may be denoted S(n) and a high-frequency component y(n) may be extracted from this signal.

According to one embodiment, the probability density function $P_{y,i}$ for obtaining the value y(n) for the high-frequency component when the mobile element is in a state I, is defined by the following expression:

$$P_{y,i}(y(n)) = \frac{1}{\sqrt{2^k}\,\sigma_{y,i}^k\,\Gamma\!\left(\frac{k}{2}\right)} y(n)^{\frac{k}{2}-1} e^{-\frac{y(n)}{2\sigma_{y,i}^2}}$$

in which:
k represents the degree of freedom of the high-frequency component equal to the number of measurement axes of said motion sensor that are taken into account;
$\sigma_{y,i}$ is a quantity proportional to the time average of the variable y(n), in the state i. For example, $\sigma_{y,i}$ is the time average of the variable y(n) divided by k; and
$\Gamma$ is the gamma function satisfying $$\Gamma\!\left(\frac{1}{2}\right) = \sqrt{\pi},\ \Gamma(1) = 1\ \text{and}\ \Gamma(z+1) = z\Gamma(z)$$

for real z.

Thus, since the data acquired is assumed to be Gaussian, there is good precision in the probability of the high-frequency component.

In one embodiment, said filter is furthermore suitable for selecting, for each measurement axis of the motion sensor, low frequencies below a second threshold equal to or below said first threshold, forming a low-frequency component of dimension equal to the number of measurement axes of the motion sensor that are taken into account Embodiments of the present invention also use a low-frequency component that enables the orientation of the sensor to be determined.

In one embodiment the probability density function for obtaining a pair of values for the low-frequency component and the high-frequency component, called the conjoint probability density function, is equal to the product of the probability density function of the low-frequency component and the probability density function of the high-frequency component previously defined, said probability density function of the low-frequency value, when the mobile element is in the state i, being defined by the following expression:

$$P_{x,i}(x(n)) = \frac{1}{\sqrt{(2\pi)^q |\Sigma_i|}} \cdot e^{-\frac{1}{2}(x(n)-\mu_{x,i})^T \Sigma_i^{-1}(x(n)-\mu_{x,i})}$$

in which:

x(n) represents the low-frequency component at the sample of index n: this is a vector of dimension q;

$\mu_{x,i}$ represents a vector of the same dimension as the low-frequency component, representative of the state of the hidden Markov model in question; and

|$\Sigma_i$| represents the absolute value of the determinant of a covariance matrix $\Sigma_i$, corresponding to the state i. When q=1, |$\Sigma_i$|=$\sigma^2_i$, the variance of x(n) for the state i.

Thus, such a system implements most applications.

According to one embodiment, the system includes display means.

Thus, the result may be easily displayed in real time or subsequently.

The mobile element EM can be a living being, whether human or animal.

In one embodiment, the system is suitable for determining the activity of the mobile element from among two states, namely a rest state and a moving state.

Thus, it is possible for a transition between two states—a rest state and a moving state—to be easily detected, at little cost, using only the high-frequency component.

According to one embodiment, the system is suitable for determining the activity of the mobile element from a set of states corresponding to various postures.

Thus, it is possible for the posture of a subject to be easily detected, at little cost, using the low-frequency and high-frequency components.

According to one embodiment, said motion sensor comprises an accelerometer and/or a magnetometer and/or gyrometer.

According to another aspect of the invention, a system is provided for determining the activity of a mobile element (EM), said mobile element with at least one motion sensor (CM) having at least one degree of freedom substantially affixed to said mobile element (EM), said system further comprising:
  a module for measuring a signal S(n) at discrete times from zero to N when the mobile element is in a state E(n);
  a module for observing a series of values q(n) which is a function of the signal S(n);
  a module for determining a list of the most likely states E($k_t$) after the calculation of:
    a probability function of q(n) when the mobile element is in the E(n) state;
    a probability function of a transition from the E(n-1) state to the E(n) state;
  probability functions of each state of the mobile element at time zero.

According to one embodiment, the probability density function for obtaining the value for the high-frequency component is defined, when the mobile element is in the state i, by the following expression:

$$P_{y,i}(y(n)) = \frac{1}{\sqrt{2^k}\,\sigma_{y,i}\Gamma\left(\frac{k}{2}\right)} y(n)^{\frac{k}{2}-1} e^{-\frac{y(n)}{2\sigma^2_{y,i}}}$$

in which:

k represents the degree of freedom of the high-frequency component equal to the number of measurement axes of said motion sensor that are taken into account;

$\sigma_{y,i}$ is a quantity proportional to the time average of the variable y(n) in the state i (for example, $\sigma_{y,i}$ is the time average of the variable y(n) divided by k); and $\Gamma$ is the gamma function satisfying $$\Gamma\left(\frac{1}{2}\right) = \sqrt{\pi},\ \Gamma(1) = 1\ \text{and}\ \Gamma(z+1) = z\Gamma(z)$$

for real z.

In one embodiment, low frequencies below a second threshold, equal to or below said first threshold, are selected, for each measurement axis of the motion sensor, and a low-frequency component of dimension equal to the number of measurement axes of the motion sensor that are taken into account is determined.

According to one embodiment low frequencies below a second threshold equal to or below said first threshold are selected for each measurement axis of the motion sensor, and a low-frequency component representing a low-frequency component of the measurement signal, along the measurement axes of the motion sensor that are taken into account, is determined.

The low-frequency component is a vector, of dimension q, denoted by x(n). A probability density function, denoted by $P_i$(x(n)) may be associated with this component for each state i in question.

BRIEF DESCRIPTION OF THE DRAWINGS

The invention will be better understood on studying a number of embodiments described by way of entirely non-limiting example and illustrated by the appended drawings in which.

DETAILED DESCRIPTION

Figure 1A:
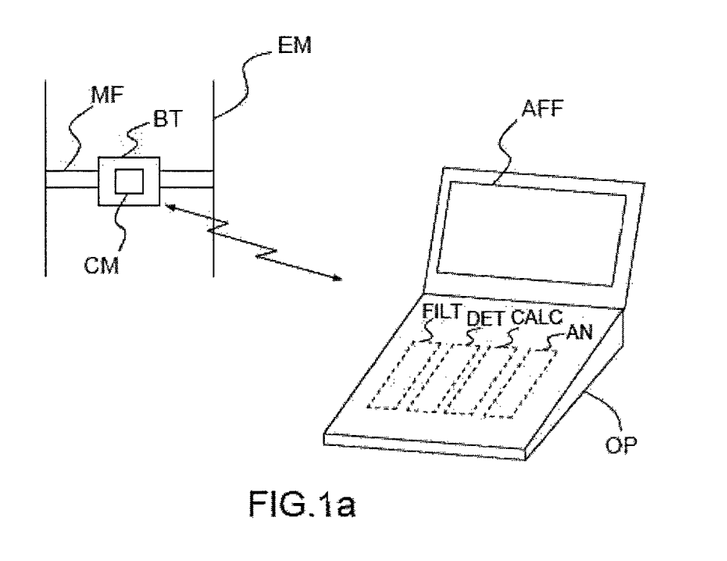
FIGS. 1a and 1b show two illustrative examples of an embodiment system for determining the activity of a mobile element.
Figure 1B:
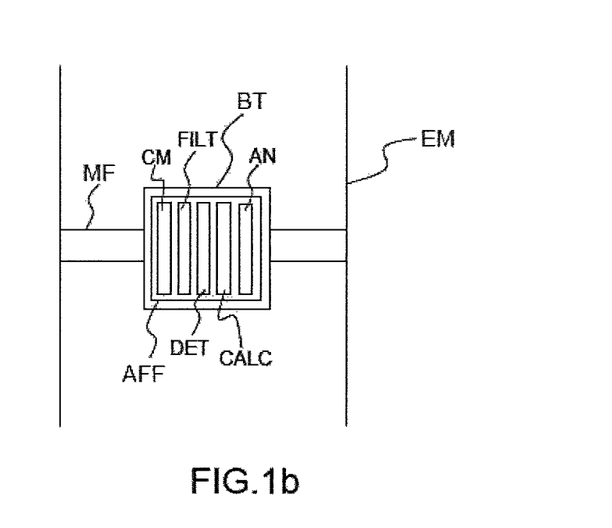

FIG. 1 shows an embodiment system for determining the activity of a mobile element EM, such as a living being, comprising at least one motion sensor CM having at least one measurement axis, inside a casing BT, provided with fastening means comprising, for example, a resilient element, for securely connecting the motion sensor CM to the mobile element EM, by means of the casing BT. The motion sensor CM may be an accelerometer, a magnetometer or a pyrometer, having one, two or three measurement axes.

The system comprises a filter FILT for selecting, for each measurement axis of the motion sensor CM, high frequencies above a threshold S. The system also comprises a module DET for determining a unidimensional high-frequency component HF equal to the square of the Euclidean norm of said high frequencies along the measurement axes of the motion sensor CM that are taken into account and a module CALC for calculating the probability of said high-frequency component, said high-frequency component being defined by a Chi-square law having a degree of freedom equal to the number of measurement axes of the motion sensor CM that are taken into account. The norm used may be the sum of the squares of the high frequencies along the measurement axes of the motion sensor that are taken into account or the square of the Euclidean norm of the high frequencies along the measurement axes of the motion sensor that are taken into account.

Analysis means AN serve for detecting oscillations or vibrations of the mobile element EM as a function of time using a hidden Markov model having 2 states corresponding respectively to the presence and to the absence of oscillations or vibrations.

A probability density function $P_y$ for obtaining the value y(n) for the high-frequency component HF is associated with each state i, said probability density function can be defined by the following expression:

$$P_{y,i}(y(n)) = \frac{1}{\sqrt{2^k}\,\sigma_{y,i}^k \Gamma\left(\frac{k}{2}\right)} y(n)^{\frac{k}{2}-1} e^{-\frac{y(n)}{2\sigma_{y,i}^2}}$$

in which expression:
k represents the degree of freedom of the high-frequency component HF equal to the number of measurement axes of said motion sensor CM that are taken into account;
$\sigma_{y,i}$ is a quantity proportional to the time average of the variable y(n), in the state i. For example, $\sigma_{y,i}$ is the time average of the variable y(n) divided by k; and
$\Gamma$ is the gamma function satisfying $$\Gamma\left(\frac{1}{2}\right) = \sqrt{\pi},\ \Gamma(1) = 1\ \text{and}\ \Gamma(z+1) = z\Gamma(z)$$

for real z.

The hidden Markov model in this case can be defined by:
a nonobserved discrete process denoting the state and taking two values: 0 when the sensor is at rest and 1 when the sensor is moving. This variable, or state, is a first-order Markov sequence, and can therefore be characterized by the probabilities of transitions from one state to another. In this case, the probability of a transition P(0;1) between the 0 state and the 1 state is chosen to be within the interval of values [0;1], for example equal to 0.1, and the probability of a transition P(1;0) between the 1 state and the 0 state is chosen to be within the interval of values [0;1], for example equal to 0.1; and
an observed process, in the present case the signal y(n); furthermore, it is desirable to define the observation probability density function according to the state, denoted by $P_{y,i}$. In this case, the probability density function can be defined by the following equation:

$$P_{y,i}(y(n)) = \frac{1}{\sqrt{2^k}\,\sigma_{y,i}^k \Gamma\left(\frac{k}{2}\right)} y(n)^{\frac{k}{2}-1} e^{-\frac{y(n)}{2\sigma_{y,i}^2}}$$

In which k=3 and $\sigma_{y,i}$ depends on the value of the state i at the instant in question. For the 0 state (sensor at rest), it is possible to choose $\sigma_y$ such that $\sigma_y \in [1\times10^{-3}; 5\times10^{-1}]$, for example $\sigma_y = 2\times10^{-1}$, and for the 1 state (sensor moving) it is possible to choose $\sigma_y$ such that $\sigma_y \in [1\times10^{-2}; 1]$, for example $\sigma_y = 1$.

At each instant n, a state of the person may then be determined as:

$$E(n) = \underset{i}{\mathrm{argmax}}(P_{y,i}(y(n)) = \underset{i}{\mathrm{argmax}}(P_i(y(n))).$$

If at the instant n the person is in the state i, then E(n)=i. $P_i(y(n))$ represents the probability density function associated with the state i of y(n) at the instant n.

Considering a vector $\theta(n)$ (for example $\theta(n)=y(n)$), combining the observed data, it is possible to write the following expression: $P_i(y(n))=Pi(\theta(n)=p(\theta(n)|E(n)=i)$, E(n) representing the state at the instant n.

However, it is not generally satisfactory to determine the state E(n) at the instant n only from the observed data y(n) and from the associated probability density functions $P_{y,i}(y(n))$. This is because having a single sample does not in general allow an attitude to be determined: it is preferable to observe several samples.

Thus, if E(0:N) denotes the series of states between the instant n=0 and the instant n=N, and if $\theta$(0:N) denotes the observed data between the instant n=0 and the instant n=N, the probability of the sequence of states E(0:N) corresponding to the sequence of states E(0), E(1) . . . E(N), also denoted by p(E(0:N)|$\Theta$(0:N-1)), is proportional to:

$$p(E(0))p(\theta(0)/E(0))\prod_{n=1}^{N} p(E(n)/E(n-1))p(\theta(n)/E(n)).$$

For example, for the sequence E(0:N)={$i_0$, . . . $i_N$}, this probability is expressed as:

$$p(E(0) = i_0)p(\theta(0) | E(0) = i_0))\prod_{n=1}^{N} p(E(n) = i_n | E(n-1) = i_{n-1})) \quad (1)$$
$$p(\theta(n) | E(n) = i_n))$$

The estimated sequence of states E(0:N) is that in which the probability is highest. In practice, rather than considering the set of all possible sequences and calculating the probability for each sequence, it may be advantageous to use a Viterbi algorithm to estimate this sequence.

P(E(0)) denotes the probability associated with the initial state E(0). For example, it is possible to choose an equiprobable distribution of each of the possible states when n=0.
p($\theta$(0)/E(0)) represents the probability of observing the data $\theta$(0) for the state E(0). This corresponds to the probability $P_i(\theta(n=0))$ with E(0)=i, which may be denoted by PE(0)($\theta$(0));
p(E(n)/E(n-1)) represents the probability of being in a state E(n) at the instant n while having been in a state E(n-1) at the instant n-1,
p($\theta$(n)/E(n)) represents the probability of observing the quantities $\theta$(n) while being in the state E(n). This corresponds to the probability $P_i(\theta(n))$ with E(n)=i.

The probabilities p(E(n)/E(n-1)) correspond to probabilities of a transition from a state E(n-1) to a state E(n). thus:
1) by establishing, for each state E(n):
the probability of observing the quantities $\theta$(n) while being in the state E(n), denoted by p($\theta$(n)/E(n));

the probability of a transition from a state E(n-1) to a state E(n), denoted by p(E(n)/E(n-1));

2) by establishing the probability associated with each state E(0); and 3) by obtaining observed values θ(n) at each instant n between n=0 and n=N, it is possible to obtain the most probable series of states E(0) . . . E(N).

Such a system makes it possible to determine at low cost the start of a movement, for example by detecting the transition from the 0 state to the 1 state.

Figure 2:
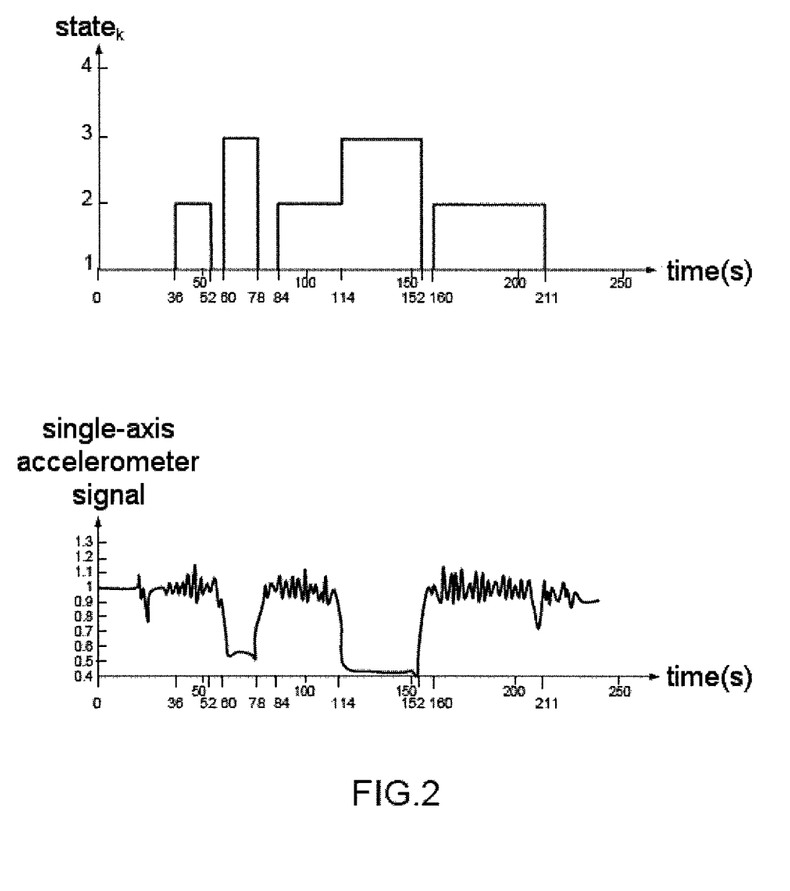
FIG. 2 shows an example of a recording by a system according to one aspect of the invention.
Figure 3:
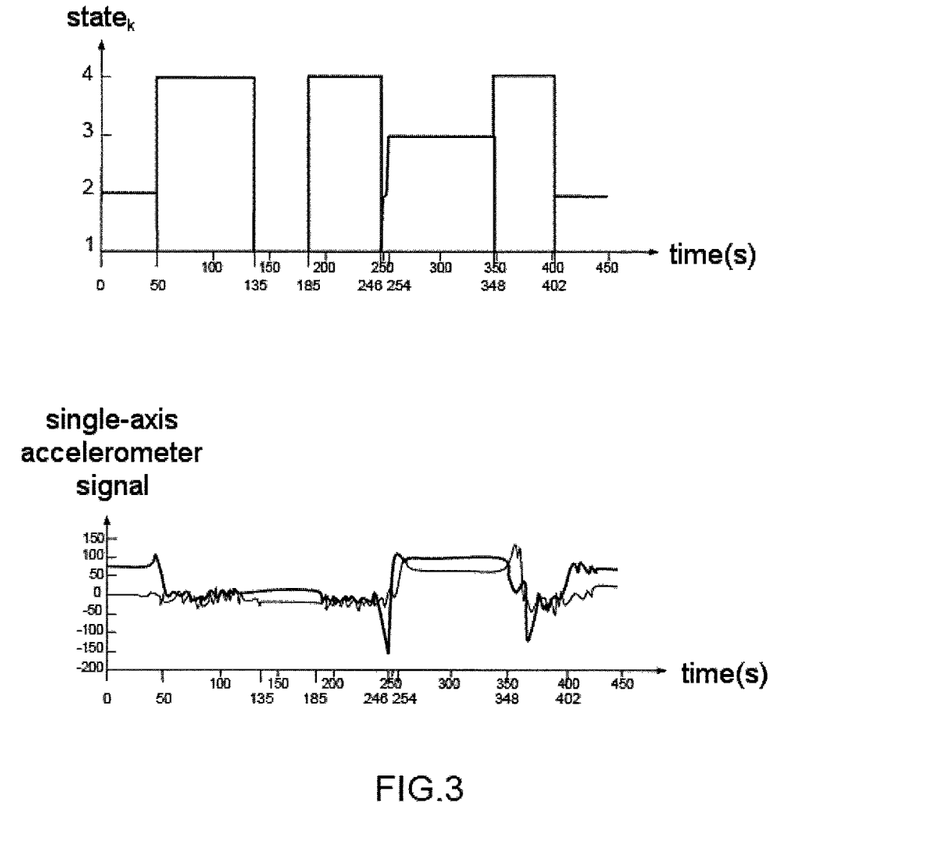
FIG. 3 shows an example of a recording by a system according to another aspect of the invention.

FIGS. 2 and 3 show recordings by systems according to two aspects of the invention, using the low-frequency components BF and the high-frequency components HF of the sensor(s) of the system.

For these two illustrative examples, the filter FILT for selecting, for each measurement axis of the motion sensor CM, high frequencies above a threshold S and low frequencies below said threshold S. As a variant, it is also possible to envisage using a first threshold S1 for selecting the high frequencies and a second threshold S2, equal to or below the first threshold S1, for selecting the low frequencies. The determination module DET is capable of determining the unidimensional high-frequency component HF equal to the square of the Euclidean norm of said high frequencies along the measurement axes of the motion sensor CM that are taken into account and a low-frequency component BF corresponding to a low-frequency signal from the motion sensor CM.

The method of obtaining x(n) when the sensor used is an accelerometer will now be explained in detail.

The signal measured by an accelerometer at an instant n may be decomposed into two summed components: S(n)=SG(n)+SP(n), where SG(n) represents the projection of the gravitational field and SP(n) represents the intrinsic acceleration of the wearer of the accelerometer.

By applying a low-pass filter to the signal S(n), the cutoff frequency being below 1 Hz, for example equal to 0.5 Hz, an estimate SG*(n) of SG(n) is obtained.

Thus, an estimate SP*(n) of SP(n) is such that SP*(n)=S(n)−SG*(n).

A low-frequency component x(n) equal to SG* at the instant n may therefore be defined.

It is possible to determine x(n) using only a single component (for example along the vertical axis), or several components Sk, of the signal S.

Again according to the example in which the sensor used is an accelerometer, it is also possible to define a high-frequency component y(n) of the signal S(n), this component being determined from SP*(n). According to a preferred embodiment, $y(n)=\|SP^*(n)\|^2$, this norm being calculated by considering one or more axes.

The calculation module CALC serves for calculating the probability density function $P_{y,i}$, corresponding to the state i, of said high-frequency component HF and the probability density function $P_{x,i}$, corresponding to the state i, of said low-frequency component BF, said high-frequency component HF being defined by a Chi-square law having one degree of freedom and said low-frequency component BF being defined by a Gaussian law.

The analysis means AN serve for determining a posture of the user as a function of time, using a hidden Markov model having N states corresponding to N postures, respectively.

The calculation module calculates, for each state, the probability density function $P_i(x(n),y(n))$ for obtaining a pair of values (x(n), y(n)), which may be called here the conjoint probability density function associated with the state i for the low-frequency component BF, and the high-frequency component HF being equal to the product of the probability density function $P_x$ of obtaining the value x(n) for the low-frequency component BF and the probability density function $P_y$ of obtaining the value y(n) for the high-frequency component HF, said probability density functions $P_{x,i}$ and $P_{y,i}$ being defined by the following expressions:

$$P_{x,i}(x(n)) = \frac{1}{\sqrt{(2\pi)^q |\Sigma_i|}} e^{-\frac{1}{2}(x(n)-\mu_{x,i})^T \Sigma_i^{-1}(x(n)-\mu_{x,i})}$$

$$P_{y,i}(y(n)) = \frac{1}{\sqrt{2^k \sigma_{y,i}^k \Gamma\left(\frac{k}{2}\right)}} y(n)^{\frac{k}{2}-1} e^{-\frac{y(n)}{2\sigma_{y,i}^2}}$$

in which:

x(n) represents the low-frequency component BF at the sample of index n;

$\mu_{x,i}$ represents a vector having the same dimension as the low-frequency component BF, representative of the state in question of the hidden Markov model;

$|\Sigma i|_i$ represents the absolute value of the determinant of the covariance matrix $\Sigma_i$ for the state i y(n) represents the sample of index n; and $\sigma_{y,i}$ is a quantity proportional to the time average of the variable y(n) in the state i. For example, $\sigma_{y,i}$ is the time average of the variable y(n) divided by k.

$P_i(x(n),y(n))$ represents the conjoint probability density function associated with the state i of x(n) and y(n) at the instant n. It corresponds here to the product of the probability density functions $P_{x,i}(x(n))$ and $P_{y,i}(y(n))$ defined above.

Considering a set θ(n), combining the observed data x(n) and y(n), the following may be written: $P_i(x(n),y(n))=P_i(\theta(n))=p(\theta(n)/E(n)=i))$, E(n) representing the state at the instant n. It will be recalled that the observed data θ(n) are obtained after the signal S(n) measured by the motion sensor CM has been processed.

However it is generally not satisfactory to determine the state E(n) at the instant n only from the observed data x(n) and y(n), and from the associated probability density functions $P_{x,i}(x(n))$ and $P_{y,i}(y(n))$, associated with these data respectively.

Experience shows that it is desirable a priori to take into account a state, for example the state E(n-1) determined during the instant n-1.

Thus, if E(0:N) denotes the series of states between the instant n=0 and the instant n=N and if θ(0:N) denotes the observed data between the instant n=0 and the instant n=N, the probability of the sequence of states E(0:N) corresponding to the sequence of states E(0), E(1) . . . E(N) can be written as:

$$p(E(0:N) | \theta(0:N-1)) \propto p(E(0))p(\theta(0)/E(0)) \prod_{n=1}^{N} p(E(n)/E(n-1))p(\theta(n)/E(n))$$

In which ∝ indicates proportionality.

For example, for the sequence $E(0:N)=\{i, i, i, \ldots, i\}$, this probability is written as:

$$p(E(0) = i)p(\theta(0) | E(0) = i))\prod_{n=1}^{N} p(E(n) = i | E(n-1) = i)) \quad (1)$$

$$p(\theta(n) | E(n) = i))$$

The estimated sequence of states $E(0:N)$ is that in which the probability is highest. In practice, rather than considering the set of all possible sequences and calculating the probability for each of them, it may be advantageous to use a Viterbi algorithm to estimate this sequence.

$P(E(0))$ denotes the probability associated with the initial state $E(0)$. For example, it is possible to choose an equiprobable distribution of each of the possible states when $n=0$.

$p(\theta(0)/E(0))$ represents the probability of observing the data $\theta(0)$ at the instant $E(0)$. This corresponds to the probability $P_i(x(n=0), y(n=0))$ with $E(n)=I$, $p(E(n)/E(n-1))$ represents the probability of being in a state $E(n)$ at the instant n, while having been in a state $E(n-1)$ at the instant n-1; and $p(\theta(n)/E(n))$ represents the probability of observing the quantities $q(n)$ while being in the state $E(n)$. This correspond to the probability $P_i(x(n),y(n))$ with $E(n)=i$.

The probabilities $p(E(n)/E(n-1))$ correspond to probabilities of a transition from a state $E(n-1)$ to a state $E(n)$. These probabilities are indicated in the following table, adopting the notations $E(n-1)=j$ and $E(n)=i$.

The series of states $E(0) \ldots E(N)$ maximizing the expression (1) may be obtained using for example the Viterbi algorithm, well known to those skilled in the art.

Thus,
1) by establishing, for each state $E(n)$:
   the probability of observing the quantities $\theta(n)$ while being in the state $E(n)$, denoted by $p(\theta(n)/E(n))$;
   the probability of a transition from a state $E(n-1)$ to a state $E(n)$, denoted by $p(E(n)/E(n-1))$;
2) by establishing the probability associated with each state $E(0)$; and
3) by obtaining observed values $\theta(n)$ at each instant n between $n=0$ and $n=N$, it is possible to obtain the most probable series of states $E(0) \ldots E(N)$.

According to this embodiment, $\theta(n)=\{x(n), y(n)\}$, $x(n)$ and $y(n)$, being respectively low-frequency and high-frequency components of the signal $S(n)$ in question at the instant n.

The system can also include a display screen AFF.

In a first example, the system comprises an accelerometer having one measurement axis and a fastening element for fastening the accelerometer to the torso of the user so that the measurement axis coincides with the vertical axis VT of the body when the user is standing upright.

According to this example, the hidden Markov model used comprises four states corresponding to four postures, namely the NTT+C or standing posture (state 1), the walking posture (state 2), the inclined posture (state 3) and the lying-down posture (state 4). The probabilities of the variables $x(n)$ and $y(n)$ associated with these states are defined by the above probabilities, with the following parameters:
   the standing of seated posture (state 1): $\mu_x=1$, $\sigma_x=0.03$, and $\sigma_y=3e^{-4}$;
   the walking posture (state 2): $\mu_x=1$, $\sigma_x=0.03$ and $\sigma_y=1.2e^{-1}$;
   the inclined posture (state 3): $\mu_x=0.5$, $\sigma_x=0.03$ and $\sigma_y=3e^{-2}$; and
   the lying-down posture (state 4): $\mu_x=0$, $\sigma_x=0.03$ and $\sigma_y=3e^{-2}$.

The probability density functions $P(\text{state}_i/\text{state}_j)$ for a transition from a state $\text{state}_i$ corresponding to one posture of the hidden Markov model to another state $\text{state}_j$ corresponding to one posture of the hidden Markov model can be the following, these being chosen so as to ensure good stability of the system:

| $P(\text{state}_i/\text{state}_j)$ | $\text{state}_i = 1$ (standing or seated) | $\text{state}_i = 2$ (walking) | $\text{state}_i = 3$ (inclined) | $\text{state}_i = 4$ (lying-down) |
|---|---|---|---|---|
| $\text{state}_i = 1$ (standing or seated) | 0.8 | 0.1 | 0 | 0.1 |
| $\text{state}_i = 2$ (walking) | 0.1 | 0.8 | 0.1 | 0 |
| $\text{state}_i = 3$ (inclined) | 0.1 | 0.1 | 0.8 | 0 |
| $\text{state}_i = 4$ (lying-down) | 0.1 | 0 | 0 | 0.9 |

The analysis module AN determines the most probable sequence of states (postures), as was described above, from:
   the signal $S(n)$ output by the sensor (from which the components $x(n)$ and $y(n)$ are extracted);
   the expression for the conjoint probability density function corresponding to each state;
   the initial conditions; and
   the probabilities of a transition between two successive states. This determination is carried out using conventional methods, for example by calculating, for the whole set of possible sequences of states, the associated probability, taking the observed signal into account, and by keeping the most probable sequence, as described for example in the document "An introduction to hidden Markov models" by L. R. Rabiner and B. H. Juang, IEEE ASSP Magazine, January 1986, or in the book "Inference in Hidden Markov Models" by Cappé, Moulines and Ryden, Springer (from the "Springer series in statistics" series).

The various elements of the system may for example be integrated into the same casing, as illustrated in FIG. 1a, or certain elements may be external, for example in a portable computer, as illustrated in FIG. 1b.

FIG. 2 illustrates an example of a recording of a user of the system of the first example, on the lower graph, and the result delivered by this system which indicates that the user was in the standing or seated posture (state 1) for 36 seconds, then in the walking posture (step 2) for 16 seconds, then in the standing or seated posture (state 1) for 8 seconds, then in the inclined posture (state 3) for 18 seconds, then in the standing or seated posture (state 1) for 6 seconds, then in the walking posture (state 2) for 30 seconds, then in the inclined posture (state 3) for 38 seconds, then in the standing or seated posture (state 1) for 8 seconds, then in the walking posture (state 2) for 51 seconds and finally ended in the standing or seated posture (state 1).

In a second example, the system comprises a first accelerometer having one measurement axis and a first fastening element for fastening the first accelerometer to the torso of the user so that the measurement axis coincides with the vertical axis VT of the body when the user is standing upright and a second accelerometer having one measurement axis and a second fastening element for fastening the second accelerometer to a thigh of the user so that the measurement axis coincides with the vertical axis VT of the body when the user is standing upright. According to this embodiment, S(n) represents the signal output by the two accelerometers at the instant n.

The hidden Markov model used can comprise four states corresponding to four postures, namely the standing posture (state 1), the seated posture (state 2), the lying-down posture (state 3) and the walking posture (state 4).

In this case, x(n) represents the pair of respective low-frequency components BF of said two accelerometers along the measurement axis coinciding with the vertical axis VT and y(n) represents the high-frequency component HF of said second accelerometer. In the example that follows, x(n) is of dimension 2.

At the sample of index n, the probability density function $P_{x,i}$ for a state i of obtaining the value x(n) is defined by the following expression:

$$P_{x,i}(x(n)) = \frac{1}{\sqrt{(2\pi)^2|\Sigma i|}} \cdot e^{-\frac{1}{2}(x(n)-\mu_x)^T \Sigma_i^{-1}(x(n)-\mu_x)}$$

in which:
Σi is a diagonal matrix of dimension 2, the first term of which is $\Sigma_{i,1}$ and the second term of which is $\Sigma_{i,2}$. This matrix describes the covariance matrix of the signal x(n) for the state i of the model; and
$\mu_{x,i}$ represents a two-component column vector representative of the state i of the model.

The probabilities of the variables x(n) and y(n) associated with these states can be defined by the above probabilities, with the following parameters:
for the standing posture (state 1), the parameters of the probability density functions can be defined as follows: $\mu_{x,1}=[1\ 1]^T$ and $$\Sigma_{x,1} = \begin{bmatrix} 0.03^2 & 0 \\ 0 & 0.03^2 \end{bmatrix}.$$

For the high-frequency component y(n), its parameter can be the following: $\sigma_{y,1}=3e^{-2}$;
for the seated posture (state 2), the parameters of the probability density functions can be defined as follows: $\mu_{x,2}=[1\ 0]^T$ and $$\Sigma_{x,2} = \begin{bmatrix} 0.03^2 & 0 \\ 0 & 0.03^2 \end{bmatrix}.$$

For the high-frequency component y(n), its parameter can be the following: $\sigma_{y,2}=3e^{-2}$;
for the lying-down posture (state 3), the parameters of the probability density functions can be defined as follows: $\mu_{x,3}=[0\ 0]^T$ and $$\Sigma_{x,3} = \begin{bmatrix} 0.03^2 & 0 \\ 0 & 0.03^2 \end{bmatrix}.$$

For the high-frequency component y(n), its parameter can be the following $\sigma_{y,3}=3e^{-2}$;
for the walking posture (state 4), the parameters of the probability density functions can be defined as follows: $\mu_{x,4}=[1\ 1]^T$ and $$\Sigma_{x,4} = \begin{bmatrix} 0.03^2 & 0 \\ 0 & 0.03^2 \end{bmatrix}.$$

For the high-frequency component y(n), its parameter can be the following: $\sigma_{y,4}=1.2e^{-1}$.

Thus, based on the above-detailed reasoning, if E(O:N) denotes the series of states between the instant n=0 and the instant n=N and if θ(0:N) denotes the observed data between the instant n=0 and the instant n=N, then E(0, N) corresponds to the sequence of states E(0), E(1) . . . E(N) that maximizes the expression:

$$p(E(0))p(\theta(0)/E(0))\prod_{n=1}^{N} p(E(n)/E(n-1))p(\theta(n)/E(n)) \quad (1)$$

According to this embodiment, θ(n)={x(n), y(n)}, x(n) and y(n) being respectively what are called low-frequency and high-frequency components of the signal S(n) measured by two accelerometers at the instant n.

The probability density functions P(state$_i$/state$_j$) for a transition from a state state$_i$ corresponding to one posture of the hidden Markov model to another state state$_j$ corresponding to one posture of the hidden Markov model can be the following, these being chosen so as to ensure good stability of the system

| P(state$_i$/state$_j$) | state$_i$ = 1 (standing) | state$_i$ = 2 (seated) | state$_i$ = 3 (lying-down) | state$_i$ = 4 (walking) |
|---|---|---|---|---|
| state$_i$ = 1 (standing) | 0.8 | 0.1 | 0 | 0.1 |
| state$_i$ = 2 (seated) | 0.1 | 0.8 | 0.1 | 0 |
| state$_i$ = 3 (lying-down) | 0.1 | 0.1 | 0.8 | 0 |
| state$_i$ = 4 (walking) | 0.1 | 0 | 0 | 0.9 |

FIG. 3 illustrates an example of a recording of a user of the system of the first example, on the lower graph and the result delivered by the system which indicates that the user was in the seated posture (state 2) for 50 seconds, then in the walking posture (state 4) for 85 seconds, then in the standing posture (state 1) for 50 seconds, then in the walking posture (state 4) for 61 seconds, then in the seated posture (state 2) for 8 seconds, then in the lying-down posture (state 3) for 94 seconds, then in the walking posture (state 4) for 54 seconds and finally ended in the seated posture (state 2).

Such a system makes it possible to determine the activity of a mobile element at a low cost and with greater precision.

In general, the method described in all these embodiments amounts to:

0) measuring the signal S(n) measured by at least one motion sensor and determining therefrom a set θ(n) of quantities observed over the course of time;

1) establishing, for at least one state E(n):
    the probability of observing the quantity θ(n) while being in the state E(n), denoted by p(θ(n)/E(n))
    the probability of a transition from a state E(n-1) to a state E(n), denoted by p(E(n)/E(n-1));
2) establishing the probability associated with each state E(0); and
3) determining the most probable series of states E(0) . . . E(N) between the instants n=0 and n=N, this series maximizing the expression:

$$p(E(0))p(\theta(0)/E(0))\prod_{n=1}^{N} p(E(n)/E(n-1))p(\theta(n)/E(n)).$$

According to the cases described above, the set of observed quantities θ(n) corresponds to a high-frequency component, denoted by y(n), obtained from the signal S(n), in other words θ(n)=y(n).

The set of observed quantities θ(n) may also combine said high-frequency component y(n) with a component x(n), the latter representing a low-frequency component of S(n). In this case, θ(n)={x(n), y(n)}.

The invention claimed is:

1. A method for determining activity of a user having a mobile element coupled thereto, the mobile element comprising at least one motion sensor comprising an accelerometer having at least two measurement axes, the method comprising:
    using the mobile element to measure movement of the user along the at least two axes to generate a corresponding signal S(n) by the motion sensor at discrete times from zero to N when the mobile element is in a state E(n) characterizing a posture of the user;
    filtering the signal S(n) to obtain a first component y(n) of high-frequency portions of the signal S(n), said high frequency portions being above a first frequency threshold on each axis of the motion sensor, and a second component x(n) of low frequency portions of the signal S(n), said low frequency portions being below a second frequency threshold lower than the first frequency threshold on at least one axis of the motion sensor;
    calculating by a processor a combination θ(n) of a norm of the first component and a contribution of the second component;
    determining by the processor a list of the most likely states E(k$_i$) characterizing the postures of the user during a period between time zero and N from a calculation of:
        a probability function of obtaining θ(n) from the signal S(n) when the mobile element is in the E(n) state;
        a probability function of a transition from the E(n-1) state to the E(n) state; and
        probability functions of each state of the mobile element at time zero; and
        outputting a most likely activity of the user as a sequence of most likely postures.

2. The method of claim 1, wherein the first component y(n) is a unidimensional component equal to a square of a norm of said high frequencies portions of the signal S(n) which are taken into account from k measurement axes of the motion sensor, and the probability function of said first component is a probability density function which is defined by a Chi-square law with a degree of freedom equal to k.

3. The method of claim 2, wherein the probability density function (P$_y$) is defined, when the mobile element is in the state i, by the following expression:

$$P_{y,i}(y(n)) = \frac{1}{\sqrt{2^k}\,\sigma_{y,i}^k \Gamma\left(\frac{k}{2}\right)} y(n)^{\frac{k}{2}-1} e^{-\frac{y(n)}{2\sigma_{y,i}^2}}$$

in which:
    σ$_{y,i}$ is a quantity proportional to a time average of the first component y(n) in the state i; and
    Γ is the gamma function satisfying $$\Gamma\left(\frac{1}{2}\right) = \sqrt{\pi},\ \Gamma(1) = 1\ \text{and}\ \Gamma(z+1) = z\Gamma(z)$$

for real z.

4. The method of claim 1, wherein the low-frequency portions are selected for each measurement axis of the motion sensor and the second component x(n) is of a dimension equal to the number of measurement axes of the motion sensor.

5. The method of claim 1, wherein the low frequency portions are selected for each measurement axis of the motion sensor and the second component x(n) is unidimensional.

6. The method of claim 1, wherein a probability density function (P(x(n),y(n))) for obtaining a pair of values ((x(n), y(n)) is calculated for the second component x(n) and the first component y(n), P(x(n),y(n)) being equal to a product of a probability density function of the second component x(n) and the probability density function of the first component y(n), said probability density function of the second component, when the mobile element (EM) is in the state i being defined by the following expression:

$$P_{x,i}(x(n)) = \frac{1}{\sqrt{(2\pi)^q |\Sigma_i|}} \cdot e^{-\frac{1}{2}(x(n)-\mu_{x,i})^T \Sigma_i^{-1}(x(n)-\mu_{x,i})}$$

in which:
    x(n) represents the second component at the sample of index n and is a vector of dimension q;
    μ$_{x,i}$ represents a vector of the same dimension as the second component, and is representative of the state of a hidden Markov model; and
    |Σ$_i$| represents the absolute value of the determinant of a covariance matrix Σ$_i$, corresponding to the state i, wherein, when q=1, |Σ$_i$|=Σ$^2_i$, the variance of x(n) for the state i.

7. A system for determining activity of a user, the system including a mobile element capable of being coupled to the user, the mobile element comprising at least one motion sensor comprising an accelerometer having at least two measurement axes, said system further comprising:
    a module to measure movement of the user along the at least two axes to generate a corresponding signal S(n) by the motion sensor at discrete times from zero to N when the mobile element is in a state E(n) characterizing a posture of the user;
    a module for filtering the signal S(n) to obtain a first component y(n) of high-frequency portions of the signal S(n), said high frequency portions being above a first frequency threshold on each axis of the motion sensor, and a second component x(n) of low frequency portions of the signal S(n), said low frequency portions being below a second frequency threshold lower than the first frequency threshold on at least one axis of the motion sensor;

a module for determining a combination θ(n) of a norm of the first component and a contribution of the second component;

a module for determining a list of the most likely states $E(k_j,)$ characterizing the postures of the user during a period between time zero and N from a calculation of:
   a probability function of obtaining θ(n) from the signal S(n) when the mobile element is in the E(n) state;
   a probability function of a transition from the E(n−1) state to the E(n) state; and
   probability functions of each state of the mobile element at time zero; and an output module configured to output a most likely activity of the user as a sequence of most likely postures.

8. The system of claim 7, further comprising:

a processor configured to calculate the first component y(n) as a unidimensional high-frequency component equal to a square of a Euclidean norm of said high frequency components along each measurement axis of the motion sensor; and a calculator configured to calculate, for each state, probability density functions of said high-frequency components, said probability density functions corresponding to each state according to a Chi-square law with a degree of freedom equal to a number k of measurement axes of the motion sensor.

* * * * *